(12) United States Patent
Neumann et al.

(10) Patent No.: US 9,119,687 B2
(45) Date of Patent: Sep. 1, 2015

(54) METHOD OF MANUFACTURING A FUNCTIONALIZED IMPLANT, AND FUNCTIONALIZED IMPLANT

(71) Applicant: DOT GmbH, Rostock (DE)

(72) Inventors: Hans-Georg Neumann, Rostock (DE); Ulrich Lembke, Rostock (DE)

(73) Assignee: DOT GmbH, Rostock (DE)

( * ) Notice: Subject to any disclaimer, the term of this patent is extended or adjusted under 35 U.S.C. 154(b) by 0 days.

(21) Appl. No.: 14/200,539

(22) Filed: Mar. 7, 2014

(65) Prior Publication Data

US 2014/0255874 A1 Sep. 11, 2014

(30) Foreign Application Priority Data

Mar. 11, 2013 (DE) .......................... 10 2013 102 370

(51) Int. Cl.
| | |
|---|---|
| *A61C 8/00* | (2006.01) |
| *A61K 6/02* | (2006.01) |
| *A61K 6/04* | (2006.01) |
| *A61K 6/06* | (2006.01) |
| *A61L 27/04* | (2006.01) |

(Continued)

(52) U.S. Cl.
CPC ............... *A61C 8/0015* (2013.01); *A61K 6/024* (2013.01); *A61K 6/0235* (2013.01); *A61K 6/04* (2013.01); *A61K 6/0643* (2013.01); *A61L 27/04* (2013.01); *A61L 27/10* (2013.01); *A61L 27/30* (2013.01); *A61L 27/50* (2013.01); *A61F 2310/00616* (2013.01); *A61F 2310/00634* (2013.01); *A61L 2400/18* (2013.01); *A61L 2420/02* (2013.01); *A61L 2430/12* (2013.01); *C23C 4/127* (2013.01)

(58) Field of Classification Search
CPC .................. A61F 2/30767; A61F 2310/00634; A61F 2310/00616; A61L 27/32; C23C 4/127
USPC .............. 427/2.26, 2.27, 180, 174, 446, 2.24, 427/337
See application file for complete search history.

(56) References Cited

U.S. PATENT DOCUMENTS 5,543,019 A * 8/1996 Lee et al. .................. 204/192.15
6,319,285 B1 * 11/2001 Chamier et al. ........... 623/22.32
(Continued)

FOREIGN PATENT DOCUMENTS

| CN | 1986003 A | * | 6/2007 |
| JP | 05057012 A | * | 3/1993 |

(Continued)

OTHER PUBLICATIONS

Khalid et al. Effect ofarccurrentonmicrostructure,texturingandwear behavior ofplasmasprayedCaZrO3 coatings.Ceramics International39(2013)2293-2302. Sep. 1, 2012.*

(Continued)

*Primary Examiner* — Cachet Sellman
(74) *Attorney, Agent, or Firm* — Klarquist Sparkman, LLP

(57) ABSTRACT

A method of manufacturing a functionalized implant, in particular a dental implant, is provided, including first providing a substrate for the implant and applying a highly porous, hydrophilic coating which contains at least one of the following materials for functionalization: zirconium or titanium or zirconium alloy or titanium alloy, zirconium oxide or titanium oxide, calcium phosphate, calcium titanate or calcium zirconate. Further provision is made for a functionalized implant, in particular a dental implant.

8 Claims, 4 Drawing Sheets

(51) Int. Cl.
*A61L 27/10* (2006.01)
*A61L 27/30* (2006.01)
*A61L 27/50* (2006.01)
*C23C 4/12* (2006.01)

(56) References Cited

U.S. PATENT DOCUMENTS

| | | | |
|---|---|---|---|
| 7,806,693 B2 * | 10/2010 | Hurson | 433/174 |
| 2003/0050705 A1 * | 3/2003 | Cueille et al. | 623/22.24 |
| 2003/0153981 A1 | 8/2003 | Wang et al. | |
| 2003/0215484 A1 * | 11/2003 | Axen et al. | 424/423 |
| 2006/0089722 A1 * | 4/2006 | Montevecchi et al. | 623/23.5 |
| 2006/0116774 A1 * | 6/2006 | Jones et al. | 623/22.32 |
| 2008/0011613 A1 * | 1/2008 | Wang | 205/318 |
| 2010/0249925 A1 * | 9/2010 | Blunn et al. | 623/11.11 |

FOREIGN PATENT DOCUMENTS

| | | |
|---|---|---|
| WO | WO2012/011878 | 1/2012 |
| WO | WO2012011878 A1 * | 1/2012 |

OTHER PUBLICATIONS

Asami et al. CaTiO3 films sputter-deposited under simultaneous Ti-ion implantation on Ti-substrate. Surface and Coatings Technology.vol. 200, Issues 1-4, Oct. 1, 2005, pp. 1005-1008.*
European Search Report for European Patent No. 14157250.3—no translation available (mailed Aug. 19, 2014).

* cited by examiner

METHOD OF MANUFACTURING A FUNCTIONALIZED IMPLANT, AND FUNCTIONALIZED IMPLANT

TECHNICAL FIELD

The present invention relates to a method of manufacturing a functionalized implant, in particular a dental implant, and to a functionalized implant.

BACKGROUND OF THE INVENTION

In the past few decades, the demands made by physicians and patients on the functionality of implants have steadily increased. In this connection the rising human life expectancy plays a decisive part since it increases the need for biocompatible medical implants. For this reason, a new generation of implants is required which have the capability of growing into the bone faster and achieving a better connection with the bone. Furthermore, modern implants of such type are required to be mechanically stable and combine with the body's own tissue in an optimum fashion within a minimum of time, accompanied by the requirement of preventing a rejection reaction or even an infection.

It is known here that an optimized adaptation in particular of the implant surface to the complex biological environment is particularly important. This adaptation is in many cases achieved by a modification of the implant surfaces, for example by a coating that allows the surface properties to be designed irrespectively of the properties of the material of the implant. Especially the surface properties of the implants are of a special significance since cell and bacterial adhesion processes are known to be highly dependent on the surface quality of the implant. In this connection, above all the chemical composition and the roughness of the surface play a significant role.

A large number of the implants currently produced are made of titanium or a titanium alloy since titanium has long stood the test as a biocompatible material. Titanium has a high mechanical strength and, furthermore, distinguishes itself by its excellent biocompatibility. A disadvantage of this material, however, is that it takes a long time until a firm connection is obtained between the bone and the implant, that is, until the implant has grown in.

It is further known that the surfaces are modified in implants that are used for orthopedic purposes, so that an optimum integration of the orthopedic implants can be attained.

Implants of the type discussed above have a metallic surface so that, for aesthetic reasons, they do not provide an optimum solution for the dental field since their coloring is distinctly different from the natural colors of the tooth or of the gums. In the event of a peri-implantitis, the implant neck may become exposed as a consequence of the receding gums, so that the dark metallic implant material will show through at that point, which is inacceptable from a cosmetic point of view.

For this reason, in the dental field implants are increasingly used which are built up of a ceramic substrate as a base body. These ceramic implant materials likewise have a high strength as well as biocompatibility. However, compared to an implant made from a titanium material, the integration of the implant into the bone is more difficult. This is primarily due to the absence of osteoconductive properties, which would facilitate the ongrowth of osteoblasts on the surface. The cell adhesion processes are therefore impaired, and a loosening of the inserted implant occurs due to an insufficient bony connection of the implant surface with the bone. This inadequate adhesion can at best be marginally improved by an additional incorporation of bone cement. Moreover, in comparison with titanium materials, the adhesion of bone cements on ceramic materials is also noticeably reduced.

A number of approaches to functionalizing an implant manufactured from a ceramic material are known from the prior art, none of which, however, provides a satisfactory result. For one thing, efforts are made to apply titanium or titanium alloys on ceramic materials to combine the advantages of both materials with each other in this way. Among other things, this is made difficult because the two materials only produce a mechanical connection, with no chemical connection being developed between the two materials. For this reason, it is necessary to first roughen the ceramic surface in order to produce as good a mechanical connection as possible between the ceramic implant and the titanium coating or titanium alloy coating.

In addition, WO 2009/036845 A1 discloses a method of applying a titanium alloy onto a ceramic substrate. The titanium alloy is applied onto the ceramic substrate by means of plasma spraying here, so that at least satisfactory adhesive tensile strengths are achieved. But the ceramic implant needed for this has an appropriate roughness which allows the adhesion of the titanium sprayed on. Therefore, in this known method a pretreatment of the ceramic material is necessary in order to ensure the required adhesive tensile strength.

The object of the present invention is to provide an improved method for the manufacture of a functionalized implant, which allows a rapid, force-fitting biologization of an implant surface.

SUMMARY OF THE INVENTION

The object is achieved according to the invention by a method of manufacturing a functionalized implant, in particular a dental implant, including the steps of providing a substrate for the implant and applying a coating which contains at least one of the following materials for functionalization: zirconium, titanium, zirconium alloy or titanium alloy, zirconium oxide or titanium oxide, calcium phosphate, calcium titanate or calcium zirconate. The method according to the invention thus allows a functionalized implant, in particular a dental implant, to be manufactured in a simpler fashion while achieving the required adhesive tensile strengths. The method is simplified to the effect that the substrate need not be pretreated (more particularly not roughened) prior to coating or application of the coating. A roughening may, however, be carried out for an improvement in the adhesive strength.

The substrate may consist of a ceramic material which is made from an ATZ ceramic or from a zirconium oxide dominated ceramic with a small addition of yttrium oxide, or which has aluminum oxide as its main component, with this ceramic material being reinforced by additions of zirconium oxide (ZTA ceramic). As an alternative, provision may also be made for a substrate that is made of metal.

By applying the high-porosity coating, a functionalization of the implant, in particular of the surface of the implant, is achieved, the functionalization being more particularly a biologization. Implants functionalized in this way have a microporous and macroporous surface which, in addition, is biocompatible with the bone tissue. The highly porous surface enhances the incorporation of or colonization by cells, which in turn accelerates the process of ingrowth of the implant. The functionalization/biologization of the implant surface is improved in that the coating provides a large free surface which leads to a rapid and complete wetting of the implant surface with body fluid, for example blood. In this way, the wettability of the surface, which constitutes an essential factor for biological activity, is considerably improved. In addition, the calcium ions present in the coating stimulate cell growth, so that ingrowth of the implant is enhanced.

In a particularly preferred embodiment, provision is made that the zirconium or titanium layer or zirconium or titanium alloy is applied by means of a PVD method. Application of this layer results in a first biologization of the implant. Applying the layer using this method is of advantage since the substrate temperatures used in this method are relatively low. This ensures that the properties of the coating and those of the ceramic substrate will not be altered in the coating process. The PVD method guarantees that an adhesively strong layer is obtained since the intrinsic energy of the layer-forming particles is sufficiently high. In the PVD process, the substrate temperature typically is <250° C., in particular <200° C. Because of the low temperature, the surface of the layer or alloy and the texture of the base material are not changed, so that the PVD process constitutes a gentle method, which does not affect the mechanical properties of the ceramic material. The layer thickness obtained in this way amounts to approximately 50 to 150 nm, in particular 80 to 100 nm.

As an alternative, it is possible to apply the zirconium or titanium layer or zirconium or titanium alloy to the substrate by means of a CVD method. The temperatures prevailing herein are, however, a good deal higher than in the PVD method, so that changes in the properties of the bond and in particular of the ceramic material/base material may possibly occur.

In an especially preferred embodiment, provision is made that the calcium phosphate layer is applied to the implant by means of an electrochemical process. The calcium phosphate layer used may, more particularly, be brushite. Brushite is an especially preferred calcium phosphate compound here because brushite is found in the natural bone and is therefore capable of stimulating the body for a short time to initiate its own bone synthesis. This accelerates the bony ingrowth of implants in particular in the primary phase. Applying the calcium phosphate layer by means of the electrochemical process makes sure that a microcrystalline, highly porous and bioactive calcium phosphate layer forms on the substrate. Compared with the plasma spraying method, the electrochemical application of the calcium phosphate, which is effected at a low temperature, provides for a higher porosity of the calcium phosphate layer while any thermally induced structural changes of the base material or of the bond of previously applied layers with it or among one another are avoided at the same time.

In particular, provision may be made here that the electrochemical process is carried out by means of an electrolysis since an electrolytic bath allows a complete covering of porous substrate surfaces and of complicated substrate geometries.

Provision is made in particular that the coated substrate is finally placed in a sodium hydroxide solution. Placement in the sodium hydroxide solution improves the osteoconductive properties of the implant since the zirconium or titanium layer or alloy reacts to form zirconium oxide or titanium dioxide. By placing the coated implant in the sodium hydroxide solution, the zirconium or titanium layers are converted to highly porous and highly hydrophilic zirconium oxide or titanium oxide layers. The sodium hydroxide solution is a 0.2-10 molar, in particular a 0.5-5 molar, solution.

A prior coating of the implant with calcium phosphate, which is performed after the deposition of the thin, dense zirconium or titanium layer, results in a formation of highly porous and highly hydrophilic calcium titanate or calcium zirconate layers when the implant is placed in the sodium hydroxide solution.

In a different embodiment, provision is made that the calcium zirconate layer is produced by spraying calcium zirconate powder on. This offers the advantage that the coating that is produced is applied to the substrate in one single method step, the spraying on of the calcium zirconate powder being performed by means of a plasma spraying method (under a vacuum or atmospherically), by high velocity oxygen fuel spraying or by a gas dynamic cold spray method, in order to ensure the high porosity of the resulting coating.

In a further embodiment, provision is made that the calcium titanate layer is produced by spraying a calcium titanate powder on. In this embodiment, too, one process step is saved in that the calcium titanate layer that develops is directly sprayed on. The two-part manufacturing process of previously coating with titanium or zirconium or a zirconium or titanium alloy and later coating with calcium phosphate by means of an electrochemical process is replaced with one method step. This is suitable in particular for implants the demands on which are different from those made on the implants manufactured in accordance with the procedure mentioned above.

The calcium titanate powder may, for example, be applied to the substrate by means of a plasma spraying method (under a vacuum or atmospherically), by high velocity oxygen fuel spraying or by a gas dynamic cold spray method.

In a further embodiment, provision is made that the calcium titanate or calcium zirconate layer is produced by depositing the calcium titanate or calcium zirconate by PVD. This embodiment presents an efficient and alternative way of providing an implant with a calcium titanate coating. In this process, the calcium titanate is applied to the substrate by means of magnetron sputtering. The coating of the substrate produced in this way again has the high porosity that is necessary in an implant which is required to grow together with the bone quickly.

Furthermore, according to the invention provision is made for a functionalized implant, in particular a dental implant, including a functionalized, adhesive coating which includes at least zirconium, titanium, an alloy including these materials, zirconium oxide or titanium oxide, a calcium phosphate layer or a calcium titanate or calcium zirconate layer for functionalizing the implant. An implant of this type distinguishes itself in that the biological activity is significantly enhanced since the coating applied is a microporous and macroporous and highly porous coating. Such a layer can only be produced by a gentle application process.

The substrate may be an oxide-ceramic substrate or a substrate made of metal.

The coating by means of a zirconium or titanium layer in accordance with the method mentioned above already constitutes a functionalization of the implant since the wettability of the surface and thus the biological activity is increased. The coating of this type has a thickness of from 50 to 150 nm.

Preferably, a functionalized coating is provided which contains a highly porous calcium phosphate layer, in particular a brushite layer. A functionalized implant having such a coating has the advantage that the ingrowth behavior of the functionalized implant is considerably improved since owing to a calcium phosphate layer (brushite) which corresponds to the early phases of bone mineralization with regard to the structure and composition and is therefore similar to that of the body, the bony ingrowth is accelerated and enhanced. This bioactive effect in the body results from the release of calcium and phosphate ions from the brushite, which are metabolized by the bone-forming cells and in this way stimulate the formation of endogenous bone tissue on the implant surface. The highly porous calcium phosphate layer can only be obtained by a coating method which does not destroy the high porosity of the calcium phosphate layer which is formed, as is the case in electrochemical layer deposition. A functionalized coating of this type includes a highly porous, microcrystalline and bioactive calcium phosphate layer which reaches a thickness of from 10 to 30 µm.

More particularly, a functionalized coating is provided which includes at least highly porous calcium titanate or calcium zirconate phases. These highly porous calcium titanate or calcium zirconate phases distinguish themselves by an acicular crystalline habit, with the calcium titanate or calcium zirconate crystals being arranged in a fleece-like manner. Thereby a large free surface is created which results in a high capillary action, so that the wetting of the implant surface can be effected more quickly and more fully. This considerably increases the osteoconductive property of the functionalized implant.

Further advantages and features will be apparent from the description below, in which a variety of exemplary and therefore non-limiting embodiments and the manufacture thereof will be described, as well as from the accompanying drawings, to which reference is made.

DETAILED DESCRIPTION

Figure 1:
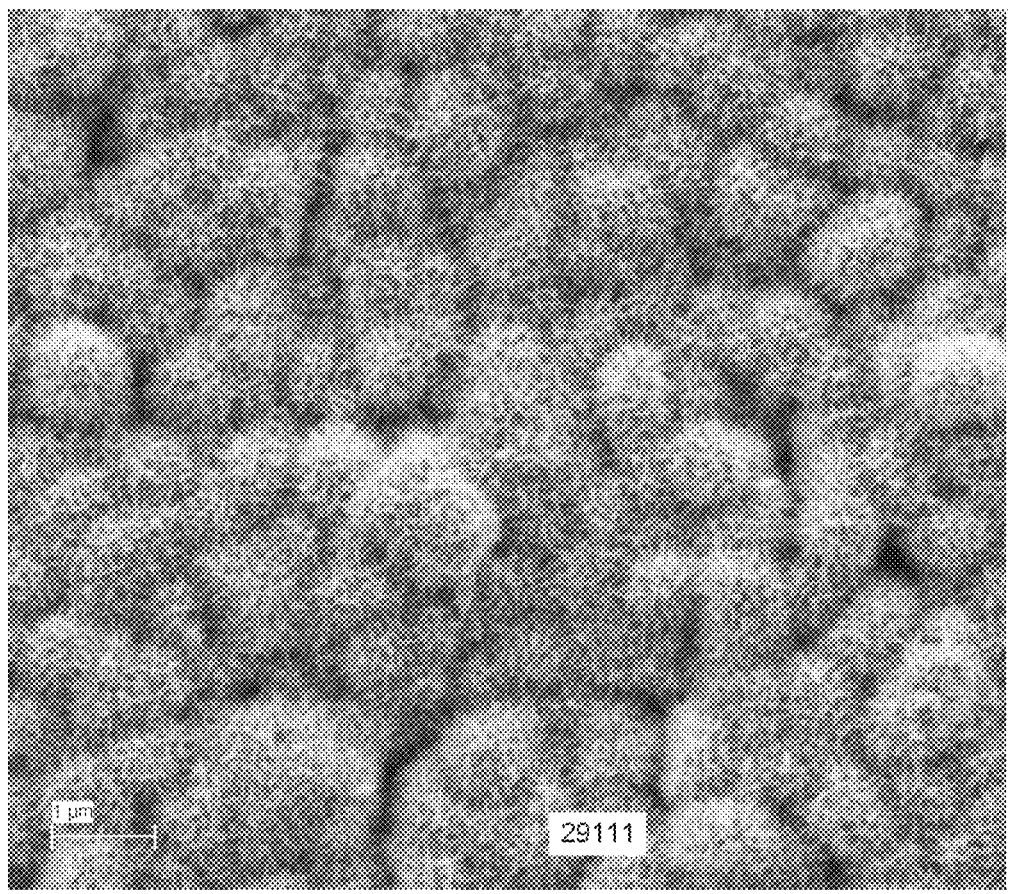
FIG. 1 shows a SEM image of a ZTA ceramic implant having a highly porous, highly hydrophilic calcium titanate layer which has been produced by means of a method according to the invention.

A first embodiment relates to a functionalized dental implant which includes a substrate manufactured from an oxide-ceramic material, the oxide-ceramic material being, for example, a ZTA ceramic (Zirconia Toughened Alumina). Such a ceramic distinguishes itself in that its main constituent is alumina, with zirconia additions being provided for strengthening. For functionalization/biologization, this substrate is provided with a titanium layer and a calcium phosphate layer, both layers being subsequently converted to a highly porous calcium titanate layer in a chemical process. An implant manufactured in this way is shown in the SEM image in FIG. 1.

Here the substrate is at first directly, i.e. without a pretreatment, provided with a titanium layer. In order that an adhesively strong coating of the substrate surface forms, the titanium layer is applied to the surface of the substrate by means of a PVD method.

This constitutes the beginning of the biologization since the wettability of the surface and therefore the biological activity is quite substantially improved even by such application of the thin layer of titanium. In this method, temperatures of less than 200° C. occur, so that there is no risk that the properties of the ceramic/coating system or the surface properties will change in the application process. In spite of the low substrate temperature, the layer-forming particles have a sufficiently high intrinsic energy to form an adhesively strong layer. The titanium layer applied in this way has a thickness of about 50 to 150 nm. The implant coated in this manner features even now a partial biologization/functionalization since the titanium layer applied in this manner considerably increases the osteoconductive properties of the surface of the implant.

In order to enhance the process of ingrowth of the implant, a calcium phosphate layer is further applied. Its micro- and macroporosity renders this calcium phosphate layer particularly well suited to accelerate the ingrowth of the implant into the bone. Moreover, the release of calcium and phosphate ions from the calcium phosphate layer promotes the osteointegration, so that a force-fitting connection is rapidly produced between the implant and the biosystem. As a result, owing to the calcium phosphate layer, the ingrowth behavior is improved or accelerated even in case of a poor bone quality. In addition, this allows a higher tolerance to micromovements. Here, the calcium phosphate layer is applied to the substrate having the titanium layer coated thereon, so that a thin, bioactive calcium phosphate layer is formed.

To manufacture a macroporous and highly porous calcium phosphate layer, the calcium phosphate is preferably applied to the conductive surface of the titanium layer by means of an electrochemical process. An electrolysis or an electrolytic bath is particularly suitable for this purpose. Brushite in particular comes into question for the calcium phosphate since it already occurs naturally in the bone and is capable of short-term stimulation of the body to synthesize its own bone, which accelerates the bony ingrowth of implants especially in the primary phase. In the further course of the ingrowth of the implant, the more readily soluble constituents of the calcium phosphate layer are then converted to the endogenous, less readily soluble hydroxylapatite.

Coating the implant with the calcium phosphate layer by means of an electrochemical process, in particular by electrolysis, results in a precipitation of calcium phosphate on the surface of the implant from the locally supersaturated electrolyte, so that a microcrystalline, highly porous and bioactive calcium phosphate layer forms on the surface. The electrolytic bath further allows to achieve a complete covering of porous implant surfaces and of complicated geometries. In addition, in contrast to a coating by means of plasma spraying methods, owing to the electrochemical process the porosity as predefined by the substrate is not reduced. Furthermore, as a result of the layer deposition at low temperatures, no changes in the structure or properties of the ceramic base material will occur when the calcium phosphate layer is applied using the electrochemical process. Therefore, owing to the electrochemical deposition of the bioactive calcium phosphate layers under near physiological conditions, an entirely new surface quality of the implant is achieved.

In the subsequent process step, the calcium phosphate layer applied to the implant in this way reacts with the underlying titanium layer in a NaOH solution to the effect that the two phases are converted to calcium titanate. The calcium titanate layer includes acicular crystallites which are arranged in a fleece-like fashion. This produces a large free surface which provides a high capillary action to the implant surface. This results in a rapid and complete wetting of the implant surface with body fluid (in particular blood), resulting in yet another increase in the biological activity. The surface quality is well visible in FIG. 1.

By way of example, the implant illustrated in FIG. 1 has been exposed to a 5 molar sodium hydroxide solution at 50° C. for 24 hours. Subsequently, the implant was rinsed and annealed at 600° C. for 1 hour to obtain the surface shown.

The calcium ions stimulating cell growth elute from the calcium titanate layer according to the invention, so that an ingrowth of the implant into its environment is expedited. In addition, cell adhesion is promoted based on the highly porous morphology of the calcium titanate layer, which, for its part, accelerates the process of ingrowth accordingly.

Figure 2:
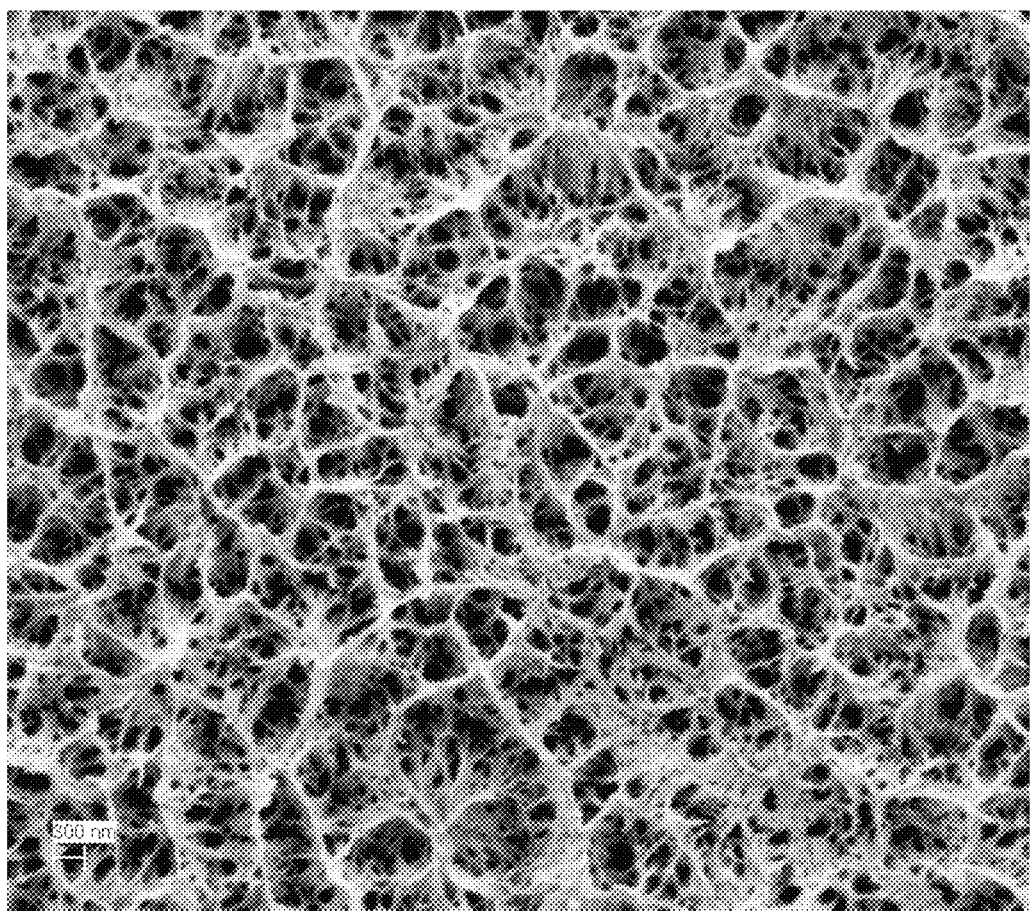
FIG. 2 shows a SEM image of a ZTA ceramic implant having a highly porous and highly hydrophilic titanium oxide layer which has been produced by means of a method according to the invention, with no calcium phosphate layer having been applied prior to the NaOH conversion.

FIG. 2 shows a SEM image of an implant which has been treated similarly to the one from the first embodiment, but in this case no calcium phosphate layer has been applied. The implant shown in FIG. 2 is a substrate made from a ZTA ceramic which has been coated with a titanium layer by means of a PVD method, analogously to the first embodiment. For a functionalization, the implant manufactured in this way has been treated with a sodium hydroxide solution, so that titanium ions present on the surface react to form titanium dioxide, as a result of which the osteoconductive properties of the surface are once more significantly enhanced. The enhancement of the osteoconductive properties is attributable to the high porosity caused by the placement in the sodium hydroxide solution.

Figure 3:
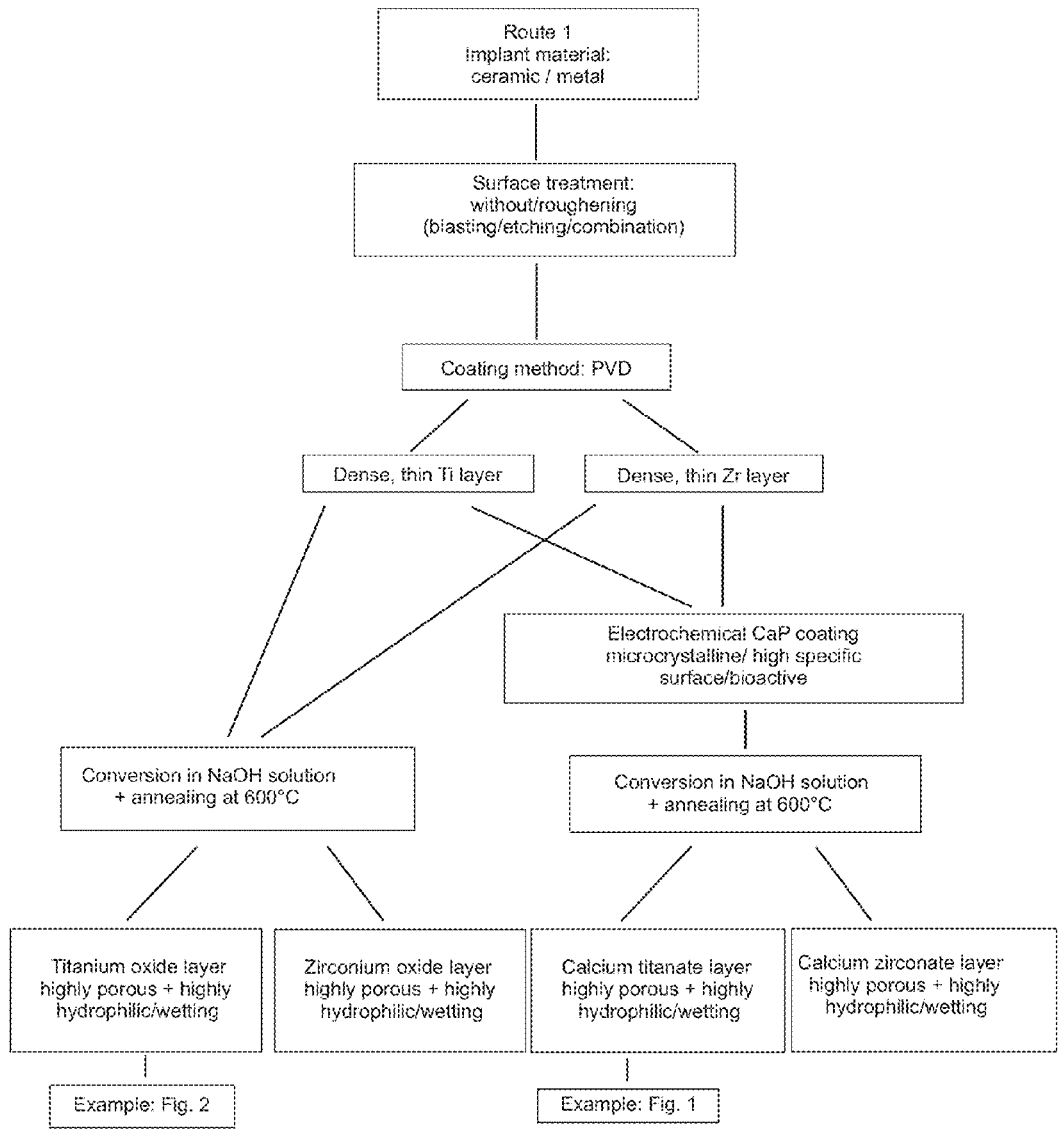
FIG. 3 shows the sequence of a method according to the invention in a first flow chart.
Figure 4:
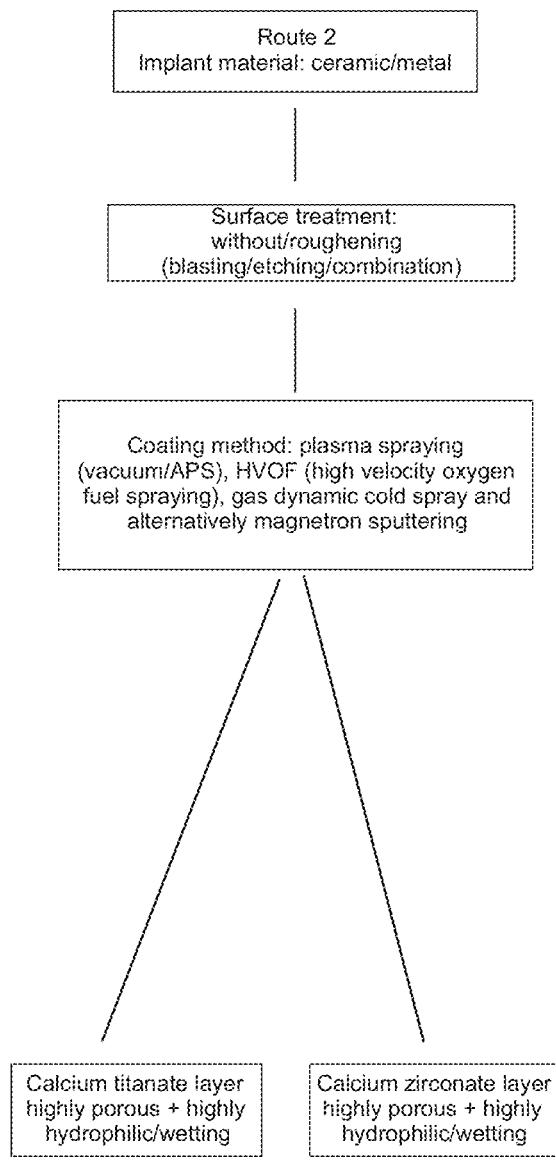
FIG. 4 shows the sequence of a further method according to the invention in a second flow chart.

The embodiments shown in FIGS. 1 and 2 are reflected in the first partial overview of FIG. 3.

Further, a substrate may be used for an implant which is made from an oxide-ceramic material which is a zirconium oxide dominated ceramic with a small addition of yttrium oxide. Generally, substrates may be used which consist of a pure or mixed oxide ceramic.

Since the substrate may have a surface of a quality which is unfavorable to the colonization by cells, the surface may be abrasively treated. This means that a roughening of the surface is effected, this being preferably accomplished by blasting with special fused alumina.

Alternatively, the rough surface may also be produced by blasting with other particles such as glass balls or hydroxylapatite, for example, and by acid etching with HF or mixed acids, or by a combination of etching and blasting.

A roughening by particle blasting should, however, be preferred since, for one thing, this is more cost-effective and, for another, simpler to realize in terms of production engineering; the residue-free removal of acid residues is a complicated process.

All of the roughening processes have in common that the substrate surface has an enlarged surface for contact with the bone, which improves the adhesion, in particular the mechanical adhesion, of further coating components.

As already described in the first exemplary embodiment, it has been found that the calcium phosphate layer applied and the underlying titanium layer are converted to calcium titanate. According to the invention, provision is therefore made that, alternatively, a calcium titanate layer is applied directly to the implant surface. This is performed, for example, by a PVD method referred to as magnetron sputtering. This method allows the developing layer to be obtained directly, with the large, free, highly porous surface which allows the capillary action and the rapid and complete wetting of the implant surface being achieved directly. In the same way, a calcium zirconate layer may be applied.

These two embodiments merely constitute exemplary embodiments of the method according to the invention and of products according to the invention obtained using the method according to the invention.

Further alternative embodiments may be obtained in that the calcium titanate or calcium zirconate is applied to the substrate by means of a plasma spraying method. The plasma spraying method may be carried out in a vacuum or under atmospheric conditions here. To this end, the calcium titanate or zirconate is introduced in powder form into a plasma flame, fused and accelerated toward the substrate, where it is deposited as a highly porous layer on the surface thereof. In these embodiments in particular, both ceramics and metals are considered for the substrate material.

Furthermore, as an alternative to the above plasma spraying method, the coating may also be applied by high velocity oxygen fuel spraying or by gas dynamic cold spraying.

All of the embodiments described have in common that a highly porous and highly hydrophilic and wetting implant surface is produced.

The embodiments according to the invention have microporous, highly hydrophilic implant surfaces in common, which are generated, for one thing, in that very thin, but dense metallic titanium or zirconium base layers are deposited on ceramic implants and are converted in NaOH to form highly porous titanium or zirconium oxide layers and, for another thing, in that prior to the NaOH treatment, brushite is further thinly deposited on the metal layers by an electrochemical deposition. In the latter case, the conversion is effected in an NaOH bath to form calcium titanate or calcium zirconate layers. This is followed by the annealing at 600° C. for improving the adhesive strength.

The other option is spray coating (plasma spraying, HVOF, gas dynamic cold spraying) with calcium titanates and calcium zirconates in the form of white, microrough, highly porous layers both on ceramic and on metallic implants.

What is claimed is:

1. A method of manufacturing a functionalized implant comprising the step of:
   a) providing a substrate for the implant wherein the substrate is selected from an ATZ ceramic, a ZTA ceramic, or a zirconium oxide dominated ceramic with an yttrium oxide addition; and
   b) applying a coating on the substrate, wherein the coating consists of a calcium zirconate layer that is applied by spraying a calcium zirconate powder onto the substrate.

2. A method of manufacturing a functionalized implant comprising the step of:
   a) providing a substrate for the implant wherein the substrate is selected from an ATZ ceramic, a ZTA ceramic, or a zirconium oxide dominated ceramic with an yttrium oxide addition; and
   b) applying a coating on the substrate wherein the coating consists of a calcium titanate layer that is applied by spraying a calcium titanate powder onto the substrate.

3. A method of manufacturing a functionalized implant comprising the steps of:
   a) providing a substrate for the implant wherein the substrate is selected from an ATZ ceramic, a ZTA ceramic, or a zirconium oxide dominated ceramic with an yttrium oxide addition; and
   b) applying a coating on the substrate, wherein the coating consists of a calcium titanate layer or a calcium zirconate layer, which layer is applied by depositing the calcium titanate or calcium zirconate by means of a PVD method.

4. A method of manufacturing a functionalized implant comprising the steps of:
   a) providing a substrate for the implant;
   b) applying a coating which contains at least one of the following materials for functionalization, onto the substrate to form a coated substrate:
      zirconium, titanium,
zirconium or titanium alloy;
c) coating the coated substrate with calcium phosphate; and
d) finally placing the coated substrate into a NaOH solution, to chemically convert the material for functionalization of the coating to calcium titanate or calcium zirconate.

5. The method according to claim 4, wherein the coating comprises a zirconium layer, a titanium layer, a zirconium alloy layer or a titanium alloy layer, wherein the layer is applied using a PVD method.

6. The method according to claim 4, wherein the coating comprises a calcium phosphate layer that is applied onto the substrate using an electrochemical process.

7. The method according to claim 4, wherein the substrate comprises an ATZ ceramic, a ZTA ceramic, or a zirconium oxide dominated ceramic with an yttrium oxide addition.

8. The method according to claim 4, characterized in that a metal is used as the substrate.

* * * * *